United States Patent
Swier

(10) Patent No.: US 11,291,814 B1
(45) Date of Patent: Apr. 5, 2022

(54) APPARATUS FOR HOLDING ROLL-ON MEDICATIONS

(71) Applicant: Ryan A. Swier, O'Fallon, MO (US)

(72) Inventor: Ryan A. Swier, O'Fallon, MO (US)

( * ) Notice: Subject to any disclaimer, the term of this patent is extended or adjusted under 35 U.S.C. 154(b) by 0 days.

(21) Appl. No.: 17/524,162

(22) Filed: Nov. 11, 2021

(51) Int. Cl.
*A61M 35/00* (2006.01)
*B25G 1/10* (2006.01)
*B25G 3/10* (2006.01)

(52) U.S. Cl.
CPC ........... *A61M 35/003* (2013.01); *B25G 1/102* (2013.01); *B25G 3/10* (2013.01)

(58) Field of Classification Search
CPC ....... A61M 35/003; B25G 1/102; B25G 3/10; A61H 7/003; B05C 17/0205; A47K 7/06; A47K 7/028
See application file for complete search history.

(56) References Cited

U.S. PATENT DOCUMENTS

| | | | |
|---|---|---|---|
| 4,571,106 A * | 2/1986 | Scuderi | A45D 34/041 |
| | | | 401/209 |
| 5,851,077 A * | 12/1998 | Trejo | A45D 34/041 |
| | | | 401/6 |
| 7,309,180 B2 * | 12/2007 | Russell | A61H 7/003 |
| | | | 401/196 |
| 8,382,727 B1 * | 2/2013 | Martin | A45D 34/041 |
| | | | 604/289 |
| D691,731 S * | 10/2013 | Grippo | A61H 39/04 |
| | | | D24/215 |
| 8,715,252 B2 * | 5/2014 | Connor | A61M 35/003 |
| | | | 604/289 |
| 8,967,898 B1 * | 3/2015 | Dayeh | A47K 7/03 |
| | | | 401/23 |
| 9,119,456 B1 | 9/2015 | Hudson | |
| 9,597,488 B1 * | 3/2017 | Jones | B25G 1/10 |
| 9,782,573 B2 * | 10/2017 | Margoosian | A61M 35/003 |
| 10,610,200 B2 * | 4/2020 | Arant | A45D 34/04 |
| 10,898,702 B2 * | 1/2021 | Beaubien | A45D 34/00 |
| 11,122,880 B1 * | 9/2021 | Blackner | A45D 34/04 |
| 11,229,924 B1 * | 1/2022 | Beltran-Felix | B05C 17/023 |
| 2007/0093736 A1 * | 4/2007 | Hebert | A61H 7/003 |
| | | | 601/135 |
| 2011/0286780 A1 * | 11/2011 | Lin | A45D 34/041 |
| | | | 401/209 |
| 2017/0113029 A1 | 4/2017 | Hernandez | |
| 2017/0334081 A1 * | 11/2017 | Dryfhout | B26B 21/44 |
| 2020/0093691 A1 * | 3/2020 | Komiyama | A61M 35/003 |
| 2020/0121899 A1 * | 4/2020 | Fox | A61M 35/003 |
| 2021/0137637 A1 * | 5/2021 | Noell | A61M 35/003 |

* cited by examiner

*Primary Examiner* — Jeffrey O'Brien
(74) *Attorney, Agent, or Firm* — Grace J. Fishel

(57) ABSTRACT

An apparatus for holding a roll-on medication applicator including a curved handle and a sleeve in which the applicator is held. The handle has upper and lower flanges supported by a web attached to the sleeve. The flanges are widened and thickened with undulations and curve over and merge at a free end of the handle. The sleeve has a closed end with an air hole and a side wall with a slit opening at an open end. The slit widens into a finger hole proximate the closed end.

10 Claims, 6 Drawing Sheets

APPARATUS FOR HOLDING ROLL-ON MEDICATIONS

BACKGROUND OF THE INVENTION

Field of the Invention

The present invention relates to an apparatus for holding a roll-on applicator for application of an analgesic or other topical medication to otherwise hard to reach areas.

Brief Description of the Prior Art

Commercially available over the counter roll-on products for topical use to alleviate pain or soreness are difficult to apply in hard-to-reach areas of the body. For example, someone experiencing lower back pain or pain in the feet or legs may have a difficult time applying the medication without assistance or undo strain and exertion. If the user lives alone, is confined to a wheelchair or bed, or has severe pain, applying a roll-on analgesic is even more difficult and stressful.

BRIEF SUMMARY OF THE INVENTION

In view of the above, it is an object of the present invention to provide an apparatus for holding a roll-on applicator that makes reaching hard-to-reach areas of the body easy. It is another object to provide an apparatus that allows the user to apply as much or little pressure on the area being treated with the roll-on applicator in those hard-to-reach areas. Other objects and features of the invention will be in part apparent and in part pointed out hereinafter.

In accordance with the invention, an apparatus for holding a roll-on medication applicator has a curved handle with upper and lower flanges supported by a web. The handle has first and second ends and the upper and lower flanges at the first end have undulations to engage a user's four fingers on upper flange and a thumb on the lower flange.

In a preferred embodiment, the upper and lower flanges and web are attached to an outside of a sleeve having a center axis, a sidewall, an open top and a closed bottom with an air hole. The upper flange is attached to the sleeve proximate the closed bottom and the lower flange is attached proximate the open top. The web is attached parallel to the center axis and the upper and lower flanges are attached perpendicular to the center axis. The sidewall of the sleeve has an inner surface dimensioned to frictionally engage an outer wall of the medication applicator and a slit opening at the open top. The slit terminates proximate the closed bottom into an enlarged aperture forming a finger hole through which the outer sidewall of the medication applicator may be accessed for use in inserting and pulling out the applicator.

In some embodiments the sleeve is cylindrical. In other cases, the handle has an arc length of about 18 inches and an arc angle of about 68 degrees. The web is about ¼ inch thick and the top and bottom flanges are about ⅝ inch wide at the second end of the handle. In another aspect, the sleeve has an outside diameter of about 1⅞ inches, a sidewall thickness of about ⅛ inch and is about 3⅜ inches long.

In other embodiments, the upper and lower flanges widen and thicken through the undulations at the first end of the handle and in some cases curve around the web at the first end of the handle and merge into each other. In still further embodiments the web of the handle at the first end includes an aperture for hanging the apparatus when not in use.

BRIEF DESCRIPTION OF THE SEVERAL VIEWS OF THE DRAWINGS

In the accompanying drawings, in which one of various possible embodiments of the invention is illustrated, corresponding reference characters refer to corresponding parts throughout the several views of the drawings in which.

DETAILED DESCRIPTION OF AT LEAST ONE PREFERRED EMBODIMENT OF THE INVENTION

Figures 5, 6:
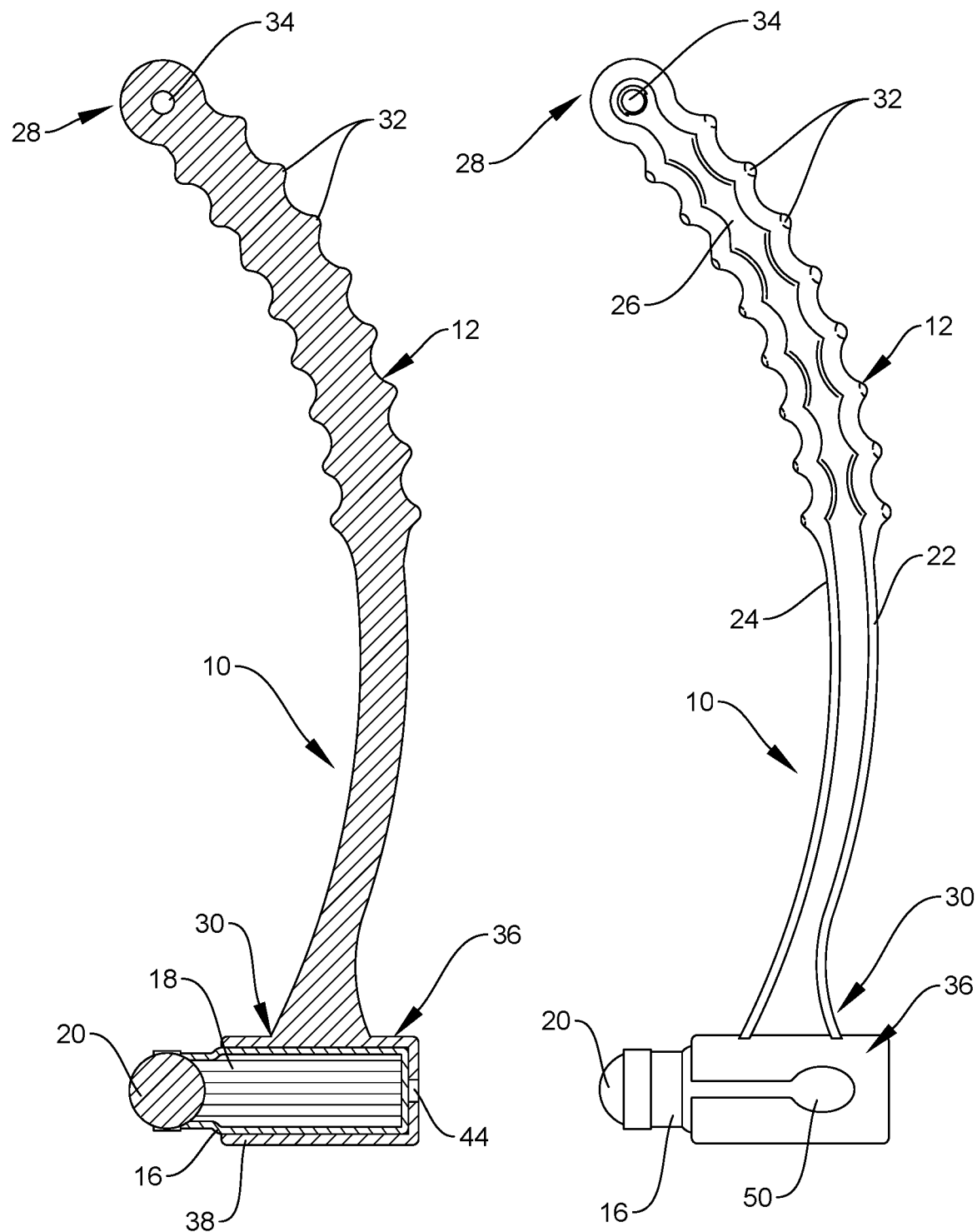
FIG. 5 is a cross-sectional view taken along the plane of 5-5 in FIG. 2.
FIG. 6 is a side elevation of the apparatus.

Referring to the drawings more particularly by reference character, an apparatus 10 is provided with an easy to use curved handle 12 that allows a user 14 to reach awkward places comfortably and easily. With specific reference to FIGS. 2-6, apparatus 10 is for use with a roll-on medication applicator 16 containing an analgesic 18 (seen in FIG. 5). Conventional roll-on applicators 16 for medications such as Icy Hot® and Bio-Freeze® are formed of plastic with an applicator rollerball 20 and come with a cap (not shown) which is removed during use. Apparatus 10 as described below may be used with such products.

Curved handle 12 has upper and lower flanges 22, 24, respectively, supported by a web 26. Apparatus 10 is preferably formed of a plastic material such as polypropylene and the I-beam structure provided by flanges 22, 24 and web 26 reduces the amount of plastic needed to mold handle 12 thereby keeping production costs low. At the same time the I-beam structure provides a strong handle that resists bending even when curved and can be used to apply medication to the area being treated together with pressure as desired.

Figures 1, 2:
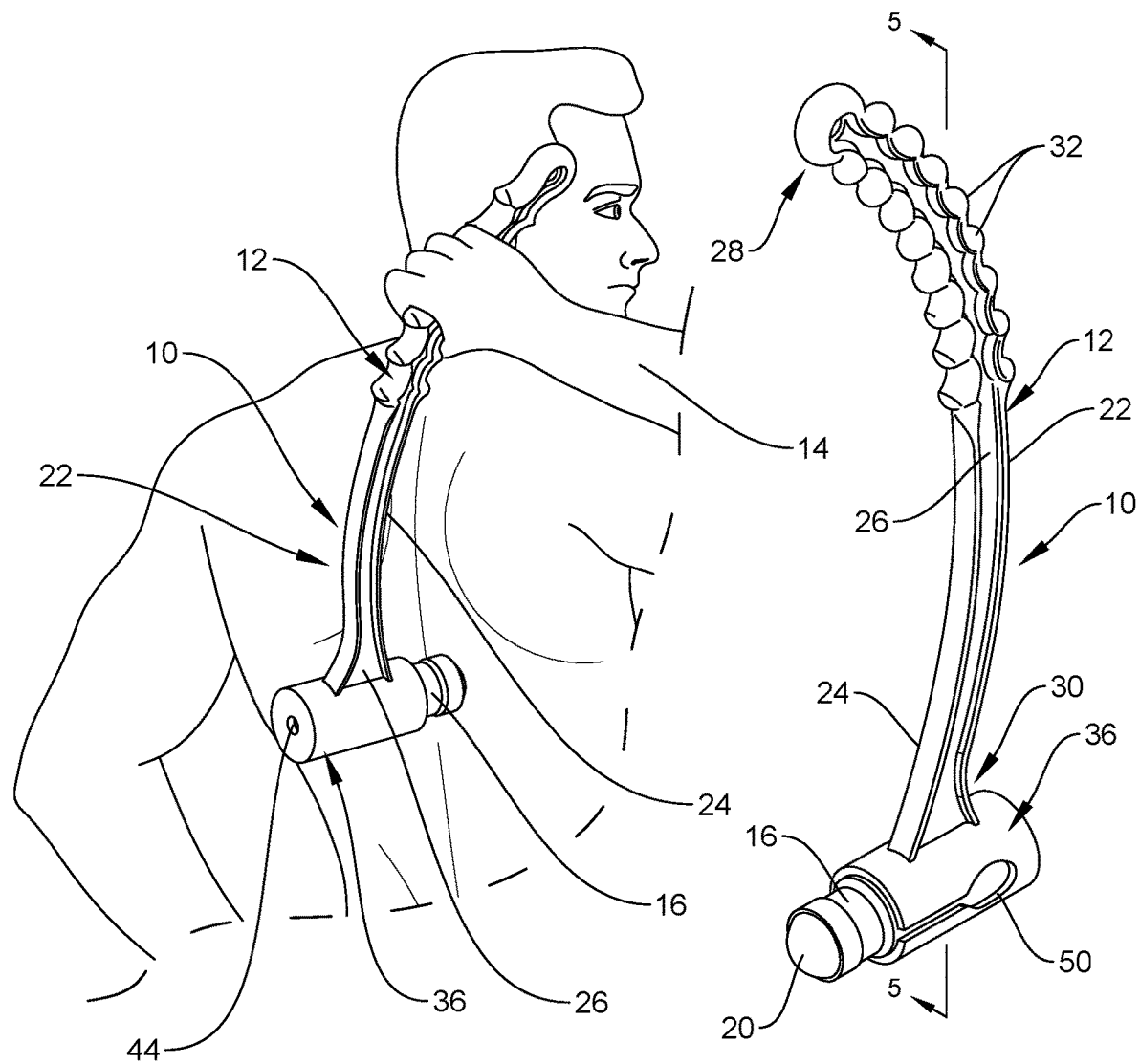
FIG. 1 is a perspective view of an apparatus in accordance with the present invention applying a medication with a roll-on applicator to a user's shoulders or upper back.
FIG. 2 is a bottom perspective view of the apparatus.
Figure 3:
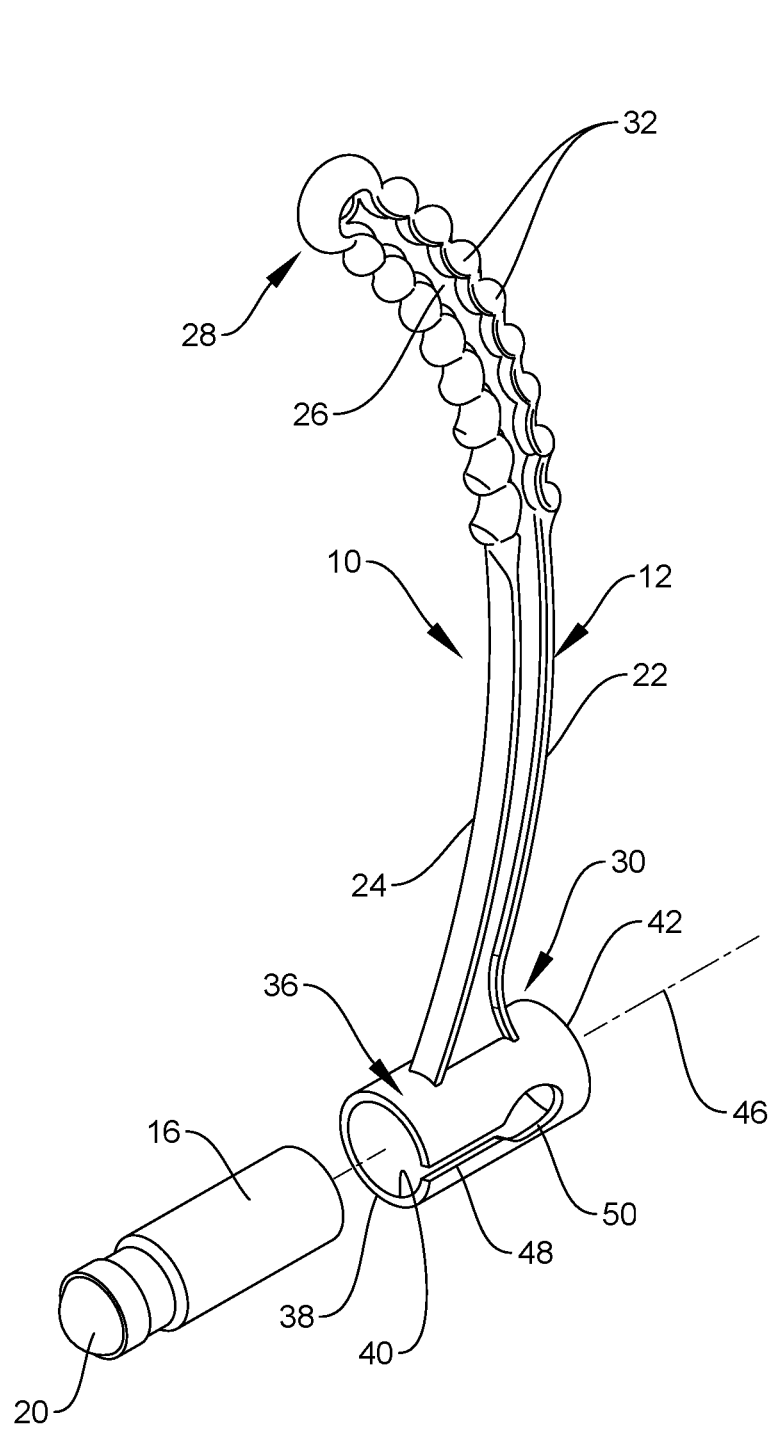
FIG. 3 is an exploded bottom perspective view showing the roll-on applicator unseated from the apparatus.
Figure 4:
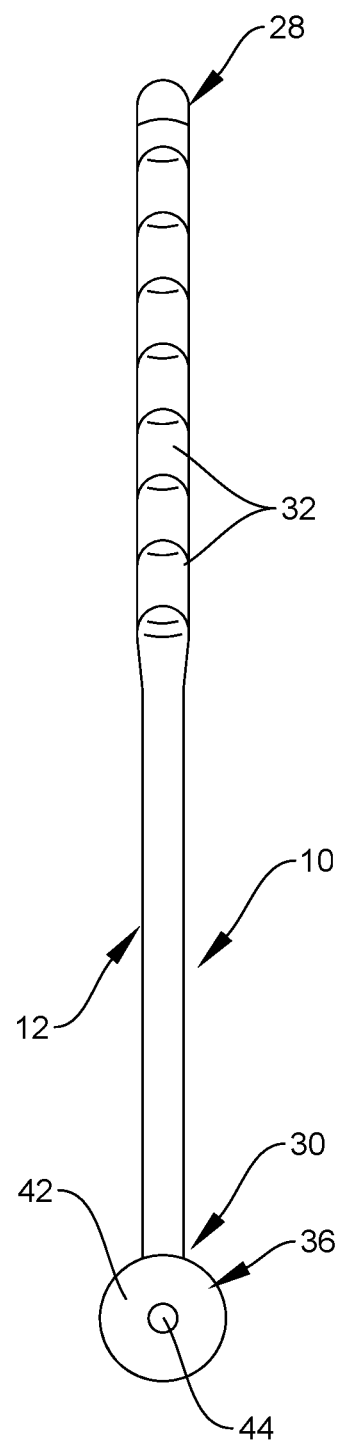
FIG. 4 is a top elevation of the apparatus.
Figure 7:
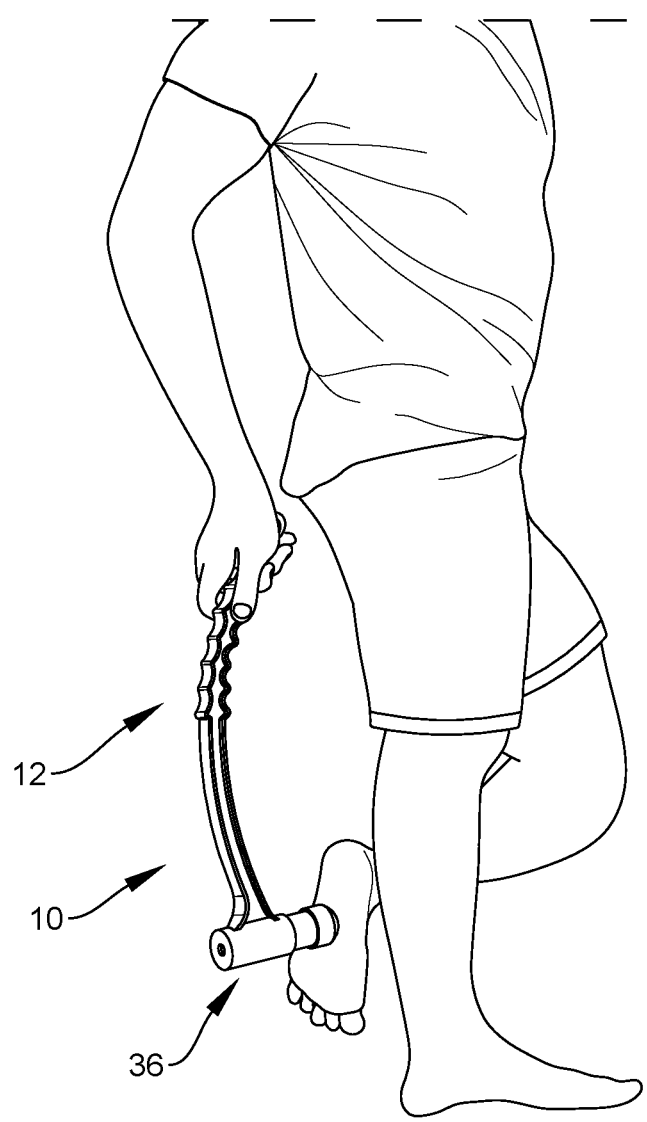
FIG. 7 is a perspective view of the apparatus applying medication to the sole of a user's foot.
Figure 8:
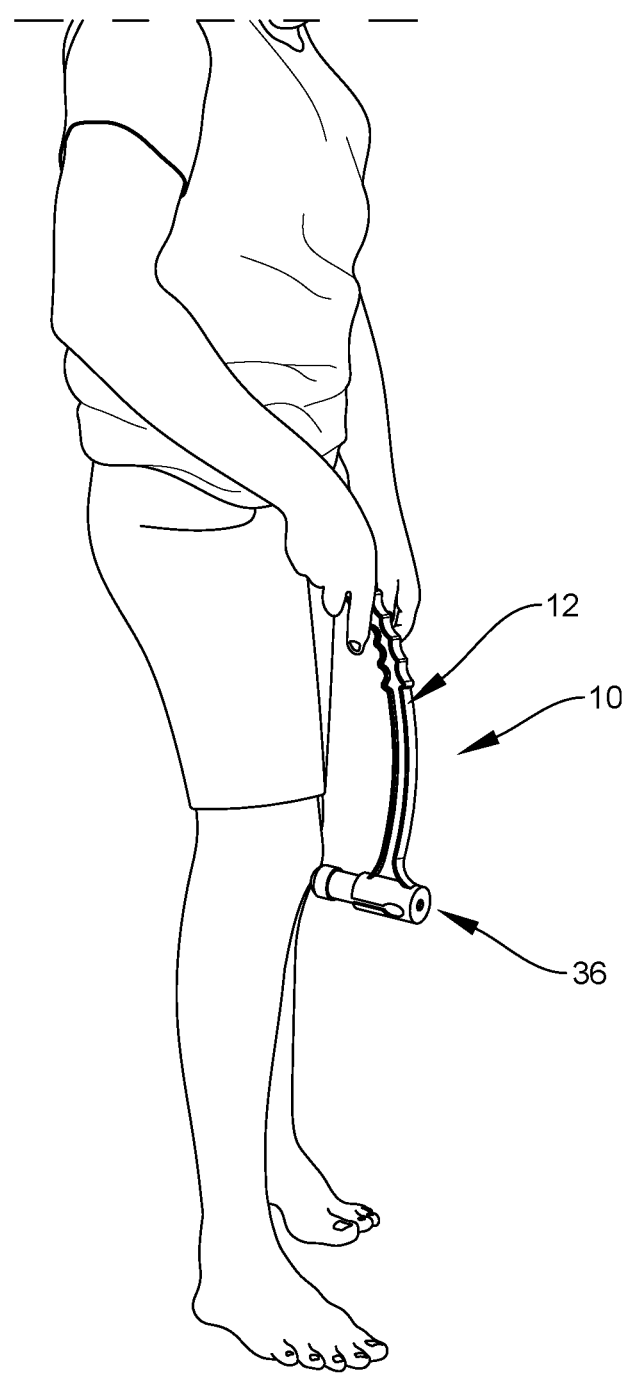
FIG. 8 is a perspective view of the apparatus applying medication to a user's knee; and, FIG. 9 is a perspective view of the apparatus applying medication to a user's lower back.
Figure 9:
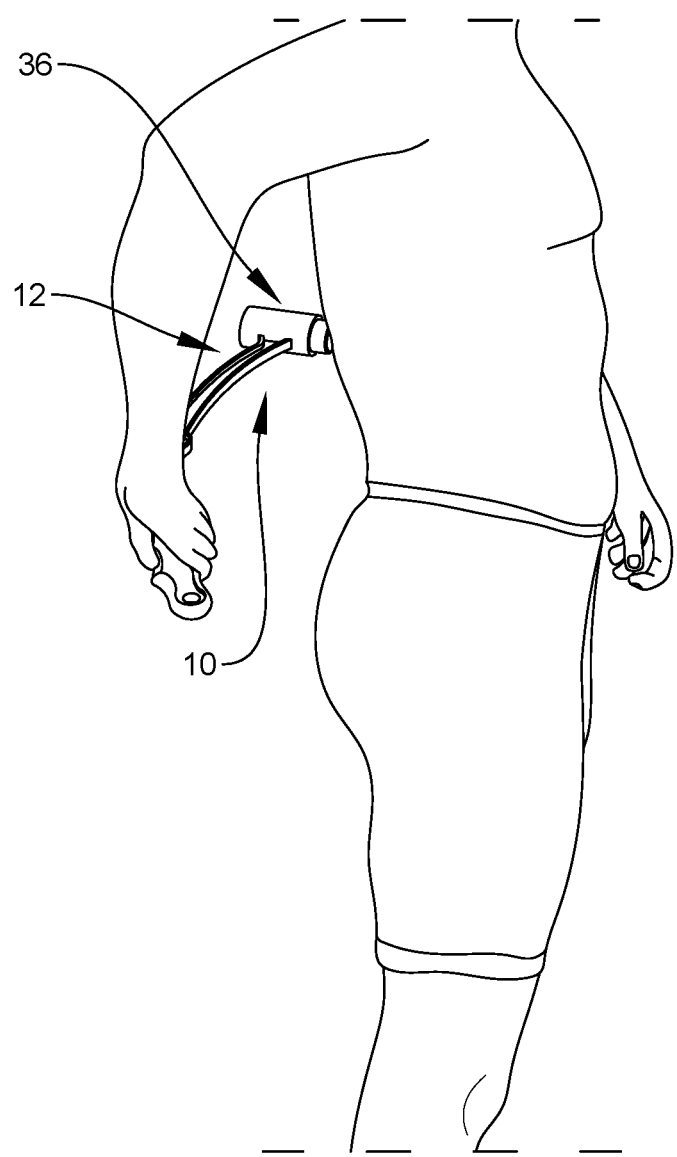

With continuing reference to FIGS. 2-6, handle 12 has a first end 28 and a second end 30 with the upper and lower flanges 22, 24 at first end 28 having undulations 32 to comfortably engage user's 14 four fingers on upper flange 22 and a thumb on lower flange 24 as seen in FIGS. 1 and 7. For reaching other areas, the position of the user's 14 four fingers and thumb on flanges 22, 24 may be reversed as shown in FIGS. 8 and 9.

In some embodiments as shown in the drawings, upper and lower flanges 22, 24 may widen and thicken through undulations 32 and may curve around web 26 at first end 28 of handle 12 and merge into each other. An aperture 34 may be provided in web 26 at first end 28 for hanging apparatus 10 when not in use.

In a preferred form curved handle 12 has an arc length of about 18 and an arc angle of about 68 degrees on a circle with a diameter of about 15 3/16 inches which may be a convenient length and arc angle for many people. It will be understood, however, that apparatus 10 may be of other lengths and arc angles. Similarly, in the illustrative but not limiting embodiment shown in the drawings, web 26 has a thickness of about 1/4 inch and upper and lower flange 22, 24 have a combined width of 5/8 inch at the second end 30.

Upper and lower flanges 22, 24 and web 26 are attached at second end 30 of handle 12 to an outside of a sleeve 36 having a sidewall 38. In the form shown in the drawings, sleeve 36 is set at about 123 degrees to handle 12. Sleeve 36 has an open top 40 and a closed bottom 42 with an air hole 44. Air hole 44 functions to break a vacuum when the applicator is removed and can be further used to assist in removal of the applicator by inserting an object such as key, pin, screwdriver or the like through the hole and pushing up on the bottom of the applicator. Upper flange 22 is attached proximate closed bottom 42 and lower flange 24 is attached proximate open top 40. Web 26 is attached parallel to a center axis 46 of sleeve 36 and upper and lower flanges 22, 24 are positioned substantially perpendicular to center axis 46.

Sidewall 38 of sleeve 36 has a slit 48 opening at open top 40 and terminating in an enlarged aperture 50 forming a finger hole. In a representative, but non-limiting embodiment, sleeve 36 is cylindrical, has an outside diameter of about 1 7/8 inch, a sidewall 38 thickness of about 1/8 inch and is about 3 3/8 inches long. In this configuration, slit 48 has a width of about 1/4 inch and widens into spoon shaped finger hole 50 having a width of 7/8 inch. Spoon shaped finger hole 50 may be used to keep the applicator from rotating while removing or putting on the applicator cap and is of use when inserting or removing the applicator from the sleeve.

In use, user 14 removes a cap (not shown) from roll-on medication applicator 16 and inserts the applicator into sleeve 36. When apparatus 10 is formed of polypropylene slit 48 allows sleeve 36 to accommodate slight differences in applicator diameters which are quite consistent across the roll-on analgesic industry. In use, applicator 16 is inverted at a slight angle (123 degrees as mentioned above) which causes product to flow smoothly on rollerball 20 and be transferred onto the treatment area. As shown in FIGS. 1 and 7-9 the curvature and length of handle 12 allows user 14 to easily reach otherwise hard to reach areas without a helper and the I-beam structure of handle 12 allows user 14 to apply as much pressure as wanted to the treatment area.

After treatment is ended, the cap may be reinstalled on applicator 16 and apparatus hung on a fastener through aperture 34 in handle 12. Applicator 16 may also be removed from sleeve 36 before apparatus 10 is stored or left in place. For this user 14 may use finger hole 50 to push applicator 16 up and out of sleeve 36 while air hole 44 prevents a vacuum forming in the bottom of the sleeve and can also be used to assist in the removal of the applicator.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. An apparatus for holding a roll-on medication applicator comprising
    a handle having upper and lower flanges supported by a web, said handle being curved and having a first and a second end, said upper and lower flanges at the first end of the handle having undulations to engage a user's four fingers on the upper flange and a thumb on the lower flange or vice versa;
    said upper and lower flanges and web attached to an outside of a sleeve having a sidewall, said sleeve having an open top and a closed bottom having an air hole, said upper flange proximate the closed bottom and said lower flange proximate the open top, said web attached parallel to a center axis of the sleeve and said upper and lower flanges attached perpendicular to the center axis of the sleeve; and,
    said sidewall of the sleeve having an inner surface dimensioned to frictionally engage an outer wall of the medication applicator, said sidewall having a slit opening at the open top, said slit terminating into an enlarged aperture forming a finger hole through which the outer sidewall of the medication applicator is configured to be accessed.

2. The apparatus of claim 1 wherein said sleeve is cylindrical.

3. The apparatus of claim 1 wherein said handle has an arc length of about 18 inches and an arc angle of about 68 degrees.

4. The apparatus of claim 1 wherein the web is about 1/4 inch thick and the upper and lower flanges are about 5/8 inch wide at the second end of the handle.

5. The apparatus of claim 2 wherein the sleeve has an outside diameter of about 1 7/8 inches, a sidewall thickness of about 1/8 inch and is about 3 3/8 inches long.

6. An apparatus for holding a roll-on medication applicator comprising
    a handle having upper and lower flanges supported by a web, said handle being curved and having a first and a second end, said upper and lower flanges at the first end of the handle having undulations to snugly engage a user's four fingers on the upper flange and a thumb on the lower flange, said upper and lower flanges widening and thickening through the undulations at the first end;
    said upper and lower flanges and web attached to an outside of a sleeve having a sidewall, said sleeve having an open top and a closed bottom having an air hole, said upper flange proximate the closed bottom and said lower flange proximate the open top, said web attached parallel to a center axis of the sleeve and said upper and lower flanges attached perpendicular to the center axis of the sleeve; and,
    said sidewall of the sleeve having an inner surface dimensioned to frictionally engage an outer wall of the medication applicator, said sidewall having a slit opening at the open top, said slit terminating into an enlarged aperture forming a finger hole through which the outer sidewall of the medication applicator is configured to be accessed.

7. The apparatus claim 6 wherein the upper and lower flanges curve around the web at the first end of the handle and merge into each other.

8. The apparatus of claim 6 wherein the web of the handle at the first end includes an aperture for hanging the apparatus when not in use.

9. The apparatus of claim 6 wherein said sleeve is cylindrical.

10. The apparatus of claim 9 wherein said handle has an arc length of about 18 inches and an arc angle of about 68 degrees.

* * * * *